United States Patent [19]

Rosenquist et al.

[11] Patent Number: 4,535,108

[45] Date of Patent: Aug. 13, 1985

[54] FLAME RETARDANT POLYCARBONATE

[75] Inventors: Niles R. Rosenquist, Evansville; John A. Tyrell, Mt. Vernon, both of Ind.

[73] Assignee: General Electric Company, Mt. Vernon, Ind.

[21] Appl. No.: 237,888

[22] Filed: Feb. 25, 1981

[51] Int. Cl.³ .................... C07C 161/00; C08K 5/42
[52] U.S. Cl. .................................. 524/162; 260/463; 560/61; 560/72; 560/109
[58] Field of Search ......... 260/463, 45.85 R, 45.7 SF, 260/505 A, 505 C, 512 C, 505 N; 560/109, 61, 72; 524/162

[56] References Cited

U.S. PATENT DOCUMENTS

| | | | |
|---|---|---|---|
| 3,272,750 | 9/1966 | Chase | 260/463 |
| 3,953,399 | 4/1976 | Mark | 260/45.85 T |
| 3,978,024 | 8/1976 | Mark | 260/45.85 T |
| 4,102,912 | 7/1978 | Carr | 260/463 |
| 4,104,217 | 8/1978 | Leistner et al. | 260/463 |

OTHER PUBLICATIONS

John D. Roberts and Marjorie C. Caserio: Basic Principles of Organic Chemistry—Second Edition, pp. 1058–1064, (1977).
CA 86, 29147q.
CA 87, 117279k.
John Roberts et al: Basic Principles of Organic Chemistry, pp. 185 and 186, (1964),
Jack Hine: Physical Organic Chemistry, pp. 5, 32 and 85–93.

Primary Examiner—Veronica P. Hoke
Attorney, Agent, or Firm—Martin B. Barancik

[57] ABSTRACT

Novel compounds of the metal salts of certain phenol ester sulfonic acids are useful as a flame retardant additive in polycarbonate composition.

20 Claims, No Drawings

4,535,108

FLAME RETARDANT POLYCARBONATE

BACKGROUND OF THE INVENTION

One of the significant problems inhibiting the further use of synthetic materials is the innate flammability of certain materials, particularly plastics. Recently, certain additives have been added to plastics which provide new compositions that have substantially increased resistance to flammability. Such a group of additives has been discovered for the polycarbonate materials. Examples of such additives are found in U.S. Pat. No. 3,978,024 which discloses the use of metal salts of phenol ester sulfonic acids in aromatic polycarbonate compositions and U.S. Pat. No. 3,953,399 which discloses the use of the metal salt of sulfonic acids of aromatic carboxylic acids and esters in aromatic polycarbonate compositions. These additives are in general very useful and have successfully extended the uses of aromatic polycarbonates into areas requiring lower levels of inflammability. However, certain properties of the aromatic polycarbonate can be detrimentally affected by the addition of these additives. The presence of the flame retardant additive can bring about a haze in transparent polymeric compositions. Furthermore, destabilization of the composition as shown by increased yellowing index values at high molding temperatures also occurs.

A new group of flame retardant additives has been discovered which maintain or less detrimentally affect the properties of the aromatic carbonate composition than some other flame retardant additives. These new additives are effective at relatively low loading levels.

SUMMARY OF THE INVENTION

In accordance with the invention, there is a new composition which comprises a polymer having a repeating unit of Formula I (see chart at last page of specification for all formulae)

wherein AR is an aromatic group in admixture with a flame retardant effective amount of a compound of the Formula II wherein R is a valence bond or an oxa group, M is an alkali or alkaline earth metal, X, Y and Z are the same or different and are hydrogen, alkyl, alkenyl, cycloalkyl, aryl, alkaryl, aralkyl, and alkoxy with the proviso that at least one of X, Y and Z is other than hydrogen.

A further aspect of the invention are compounds of Formula II wherein R, M, X, Y and Z are defined as above.

Another aspect of the invention is the process for preparing a compound of Formula II which comprises reacting a compound of Formula IV with a compound of Formula V wherein W is a metal ion and R, M, X, Y and Z are defined as above; in the presence of water, an organic solvent which solubilizes the Formula IV reactant and an effective amount of amine catalyst.

DETAILED DESCRIPTION OF THE INVENTION

The phenyl ester sulfonic acid salt flame retardant additives of this invention are preferably of the Formula II structure wherein X, Y and Z have the following meanings: alkyl is one to about twelve carbon atoms, inclusive; alkenyl is two to about twelve carbon atoms, inclusive; cycloalkyl is of about five to eight carbon atoms, inclusive; aryl is phenyl; aralkyl is phenyl substituted alkyl of one to six carbon atoms, inclusive; alkaryl is alkyl substituted phenyl wherein alkyl is one to six carbon atoms, inclusive; and alkoxy is of one to twelve carbon atoms, inclusive. A more preferred group of substituents include alkyl and alkenyl, each with a maximum of about six carbon atoms, inclusive.

A further preferred group is where $SO_3M$ is at the 4-position. When used in the specification and claims, alkyl and alkenyl include branched as well as straight chain moieties, for example methyl, ethyl, propyl, isopropyl, n-butyl, tert butyl, n-pentyl, neopentyl, isohexyl, 2,4-dimethylpentyl, isooctane, 3-isopropylhexyl, n-decyl, isoundecyl, 2,4-diethyloctyl, propylenyl, 1-butene, isopenten-1-yl, hepten-3-yl, 2-isobutylhexen-4-yl, and dodecen-2-yl.

Examples of cycloalkyl are cyclopentyl, cyclohexyl, cycloheptyl and cyclooctyl. Examples of aryl substituted alkyl include benzyl, phenethyl and phenbutyl. Examples of alkaryl are tolyl, ethylbenzenyl, cumyl and the like.

Examples of alkali and alkaline earth metals include sodium, potassium, calcium and barium. Alkali metals are preferred. Of the generally employed alkali metals, potassium is preferred because of its reduced propensity to cause haze.

Examples of metal ions which are useful in W in Formula V are sodium, potassium and calcium.

Flame retardant additives of the invention wherein R is a valence bond are represented by Formula VI while those additives wherein R is an oxa group are represented by Formula VII.

The flame retardant additives of this invention are simply prepared and with a minimum of contamination by reacting a compound of Formula IV with a compound of Formula V in the presence of water, an organic solvent which solubilizes the Formula IV reactant and an effective amount of an amine catalyst.

The reactants are readily prepared by methods known in the art. The compounds of Formula IV, substituted phenyl acid chlorides, are well known or readily prepared. The compounds of Formula V, metal phenolate sulfonic acid salts, are also readily prepared from the phenol sulfonic acids.

The organic solvent employed is any of the organic solvents employed in the interfacial polymerization process for preparing high molecular weight aromatic polycarbonate, for example, the halogenated hydrocarbons. The preferred solvent is methylene chloride.

The catalyst employed is any of the catalysts useful in the interfacial polymerization process for preparing high molecular weight aromatic polycarbonate. The preferred catalyst is triethylamine.

The temperature of the reaction is not unduly significant. Temperatures of from about 10° to about 60° C., preferably from about 20° to about 40° C. can be employed.

The composition of the invention is simply prepared by adding a flame retardant effective amount of an additive of Formula II to the polymer having a repeating unit of Formula I. This addition can be made to the powder prior to extruding or during the melt stage.

An effective flame retardant amount of the additive is employed. Flame retardancy with quantities as low as 0.0025 or even lower can be observed, although it is preferable to use a quantity of about 0.005 or higher. The more additive in the composition, the greater the negative effect on the transparency of the polymer and the yellowing index; however, the greater flame retardancy also shown. Therefore, the maximum amount of additive is dependent upon the characteristics required in the specific polycarbonate application. All percentages are based on weight percent of the polymer.

The polymer to which the additive is added is prepared in the conventional manner by reacting a dihydric phenol with a carbonate precursor in an interfacial polymerization process. Typical of some of the dihydric phenols that may be employed in the practice of this invention are bisphenol-A, (2,2-bis(4-hydroxy-3-methylphenyl) propane, 4,4-bis(4-hydroxyphenyl) heptane, 2,2-(3,5,3',5'-tetrachloro-4,4'-dihydroxydiphenyl) propane, 2,2-(3,5,3',5'-tetrabromo-4,4'-dihydroxydiphenyl)propane, (3,3'-dichloro-4,4'-dihydroxyphenyl) methane, bis 4-hydroxy phenyl sulfone and bis 4-hydroxy phenyl sulfide. Other dihydric phenols of the bisphenol type are also available and are disclosed in U.S. Pat. Nos. 2,999,835; 3,028,365 and 3,334,154. Bisphenol-A is preferred.

It is, of course possible to employ two or more different dihydric phenols or a copolymer of a dihydric phenol with a glycol or with hydroxy or acid terminated polyester, or with a dibasic acid in the event a carbonate copolymer or interpolymer rather than a homopolymer is desired for use in the preparation of the aromatic carbonate polymers of this invention. Also employed in the practice of this invention may be blends of any of the above materials to provide the aromatic carbonate polymer.

The carbonate precursor may be either a carbonyl halide, a carbonate ester or a haloformate. The carbonyl halides which can be employed herein are carbonyl bromide, carbonyl chloride and mixtures thereof. Typical of the carbonate esters which may be employed herein are diphenyl carbonate, di-(halophenyl) carbonates such as di-(chlorophenyl) carbonate, di-(bromophenyl) carbonate, di-(trichlorophenyl) carbonate, di(tribromophenyl) carbonate, etc., di-(alkylphenyl) carbonate such as di(tolyl) carbonate, etc., di-(naphthyl) carbonate, di-(chloronaphthyl) carbonate, phenyl tolyl carbonate, chlorophenyl chloronaphthyl carbonate, etc., or mixtures thereof. The haloformates suitable for use herein include bis-haloformates of dihydric phenols (bischloroformates of hydroquinone), or glycols (bishaloformates of ethylene glycol, neopentyl glycol, polyethylene glycol, etc.). While other carbonate precursors will occur to those skilled in the art, carbonyl chloride, also known as phosgene, is preferred.

The polymers of this invention may be prepared by employing a molecular weight regulator, an acid acceptor and a catalyst. The molecular weight regulators which can be employed in carrying out the process of this invention include monohydric phenols such as phenol, chroman-1, paratertiarybutylphenol, parabromophenol, primary and secondary amines, etc. Preferably, phenol is employed as the molecular weight regulator.

A suitable acid acceptor may be either an organic or an inorganic acid acceptor. A suitable organic acid acceptor is a tertiary amine and includes such materials as pyridine, triethylamine, dimethylaniline, tributylamine, etc. The inorganic acid acceptor may be one which can be either a hydroxide, a carbonate, a bicarbonate, or a phosphate of an alkali or alkaline earth metal.

The catalysts which are employed herein can be any of the suitable catalysts that aid the polymerization of bisphenol-A with phosgene. Suitable catalysts include tertiary amines such as, for example, triethylamine, tripropylamine, N,N-dimethylaniline, quaternary ammonium compounds such as, for example, tetraethylammonium bromide, cetyl triethyl ammonium bromide, tetra-n-heptylammonium iodide, tetra-n-propyl ammonium bromide, tetramethylammonium chloride, tetramethyl ammonium hydroxide, tetra-n-butylammonium iodide, benzyltrimethylammonium chloride and quaternary phosphonium compounds such as, for example, n-butyltriphenyl phosphonium bromide and methyltriphenyl phosphonium bromide.

Also included herein are branched polymers wherein a polyfunctional aromatic compound is reacted with the dihydric phenol and carbonate precursor to provide a thermoplastic randomly branched polycarbonate polymer.

These polyfunctional aromatic compounds contain at least three functional groups which are carboxyl, carboxylic anhydride, haloformyl or mixtures thereof. Examples of these polyfunctional aromatic compounds which may be employed in the practice of this invention include: trimellitic anhydride, trimellitic acid, trimellityl trichloride, 4-chloroformyl phthalic anhydride, pyromellitic acid, pyromellitic dianhydride, mellitic acid, mellitic anhydride, trimesic acid, benzophenonetetracarboxylic acid, benzophenonetetracarboxylic anhydride and the like. The preferred polyfunctional aromatic compounds are trimellitic anhydride or trimellitic acid, or their haloformyl derivatives.

Also, included herein are blends of a linear polymer and a branched polymer.

The following examples are intended to illustrate the invention and are not intended to narrow the broad inventive concept.

EXAMPLE 1

A. Preparation of compound 1 (R is oxa; X=Y=Z=H; $SO_3M$ is at the 4-position and M is potassium). In a 500 ml 3-neck round bottom flask fitted with a dropping funnel and containing a magnetic stir bar were mixed 21.2 g (0.1 mole) of the potassium salt of phenol sulfonic acid, 5.6 g of potassium hydroxide and 75 ml distilled water. The mixture was stirred until all solids were dissolved, then 75 ml methylene chloride and 1.0 ml triethylamine were added. With vigorous stirring, 15.6 g (0.1 mole) of phenyl chloroformate dissolved in 15 ml methylene chloride were added dropwise over 15 minutes to the flask. A white precipitate formed.

During the addition of the chloroformate, an additional 25 ml water and 25 ml methylene chloride were added and the reaction mixture was occasionally stirred manually in order to insure thorough mixing of the reactants. The resultant slurry was then stirred for an additional 15 minutes, with occasional manual stirring to break up lumps of precipitate. The precipitate was then collected by filtration. The mixture was then stirred with 100 ml methylene chloride and the methylene chloride then removed by filtration. This was repeated. The solids were then washed with 50 ml additional methylene chloride. The solids were then dried in a vacuum dessicator. Yield was 24 grams. The product was then recrystallized from water.

It is important that the solid be free of unreacted chloroformate or acid chloride at the time of re-crystallization. In some cases additional washing of the solid after drying should be performed.

B. In like manner as in Example 1A, compounds 2 through 7 of the Table below were prepared.

C. Preparation of compound 8 (R is oxa; Y=4-cumyl, X=Z=H; SO$_3$M is at the 4-position; M is potassium). In a 500 ml 3-neck round bottom flask fitted with a dropping funnel and containing a magnetic stir bar were mixed 21.2 g (0.1 mole) of the potassium salt of phenol sulfonic acid, 5.6 g of potassium hydroxide and 40 ml distilled water. The mixture was stirred until all solids were dissolved, then 50 ml methylene chloride and 0.6 ml triethylamine were added. With vigorous stirring, 27.5 g (0.1 mole) of 4-cumyl phenol chloroformate was added over 3 minutes to the flask. The reaction mixture converted to a thick creamy white emulsion. The emulsion was stirred for an additional 15 minutes. The methylene chloride was then removed under vacuum. (The vacuum was applied gradually to control foaming.) To the resultant aqueous slurry was added 250 ml additional water. The mixture was heated to 60° C., filtered, then cooled until the water was partially frozen. The reaction product precipitated as a thick paste on the bottom of the flask. The aqueous slush was decanted off. To the paste was added 50 ml distilled water. Upon warming to 35° C. with stirring, the paste dispersed to yield a translucent uniform mixture. Upon cooling again to the freezing point, the product formed as a paste and was isolated by decanting off the water and drying in a vacuum dessicator.

D. In like manner as in C above, compound 9 of the Table was prepared.

E. Compounds 1-9 are specific examples of Formula II except that both 1 and 2 are unsubstituted at Y as well as X and Z. For compounds 3-9 X and Z are hydrogen, SO$_3$M is at the 4-position and M is potassium.

TABLE 1

| COMPOUND | STRUCTURE R | Y | IR$_{cm}^{-1}$ |
| --- | --- | --- | --- |
| 1 | oxa | H | 1775; |
| 2 | valence bond | H | 1745; 1150 to 1225 |
| 3 | valence bond | 2-CH$_3$ | 1740; 1175 to 1260 |
| 4 | valence bond | 3-CH$_3$ | 1745; 1150 to 1225 |
| 5 | valence bond | 4-CH$_3$ | 1735; 1175 to 1230 |
| 6 | valence bond | 4-tert C$_4$H$_9$ | 1740; 1175 to 1250 |
| 7 | oxa | 4-tert C$_4$H$_9$ | 1175; 1180 to 1275 |
| 8 | oxa | 4-cumyl | 1170; 1160 to 1370 |
| 9 | oxa | 4-1,1,3,3-tetramethyl butyl | 1780; 1180 to 1275 |

Compounds 1 and 2 are both known compounds. Chemical Abstracts references for compound 1 are 65 PC17120d and U.S. Pat. No. 3,272,750 and for compound 2 are 87 117279k and 86 29147q.

PMR spectra are run on all the compounds and are consistent with the assigned structures.

EXAMPLE 2

To a bisphenol-A polycarbonate resin is added about 0.1 part by weight per hundred parts by weight of resin of a phosphite color stabilizer mixed with an epoxy stabilizer. A portion of the stabilized resin is set aside as the control and varying amounts of flame retardant compounds identified as compounds 1-9 of the table are added to the resin. This stabilized resin product is then fed to an extruder operating at a temperature of about 500° F. to extrude the resin into strands and the extruded strands are chopped into pellets. The pellets are then injection molded at about 570° F. into test bars measuring about $2\frac{1}{2}"\times\frac{1}{2}"\times\frac{1}{8}"$ and into test plaques measuring $3"\times2"$ with thickness of $\frac{1}{8}"$ over $2"\times2"$ of the surface and thickness of 1/16" over $1"\times2"$ of the surface.

Flame retardancy is observed in the test bars with the compounds at each weight level tested.

The test plaques were used for the % haze and Yellowness Index (YI) tests. The % haze was determined by ASTM D1003 on the 125 mil ($\frac{1}{8}"$ thick parts) on a Pivotal-sphere Hazemeter made by Gardner Lab Inc., Bethesda, Md. The YI was determined by ASTM D1925 on $\frac{1}{8}"$ thick parts on a Model XL-23 colorimeter made by Gardner Lab Inc., above. Below are the results.

TABLE 2

| FLAME RETARDANT COMPOUND | QUANTITY WT. % | % HAZE | YI |
| --- | --- | --- | --- |
| Control* (no flame retardant additive) | — | 0.4 | 3.0 |
| 1 | 0.01 | 0.5 | 2.7 |
|  | 0.05 | 2.5 | 4.3 |
| 2 | 0.0095 | 1.9 | 3.4 |
|  | 0.016 | 3.9 | 3.1 |
|  | 0.047 | 14.4 | 4.6 |
| 3 | 0.01 | 0.8 | 2.3 |
|  | 0.0165 | 1.1 | 2.5 |
|  | 0.05 | 5.8 | 4.3 |
| 4 | 0.01 | 1.3 | 2.5 |
|  | 0.0165 | 2.1 | 2.4 |
|  | 0.05 | 9.1 | 3.3 |
| 5 | 0.01 | 1.2 | 2.9 |
|  | 0.0165 | 2.2 | 3.2 |
|  | 0.05 | 10.0 | 6.7 |
| 6 | 0.011 | 0.5 | 2.7 |
|  | 0.056 | 6.0 | 6.3 |
| 7 | 0.012 | 0.4 | 2.9 |
|  | 0.06 | 1.2 | 4.5 |
| 8 | 0.07 | 0.4 | 3.5 |
|  | 0.1 | 0.5 | 3.7 |
| 9 | 0.1 | 0.9 | 4.6 |

*Typically, controls vary over a range of 0.4 to 0.8 in % haze and 2.7 to 3.3 in YI.

As is observed from the results of the Table 2, the substituted phenol ester sulfonic acid salts, with R being either a valence bond or a oxa group all have lower percent haze and/or lower yellowness indices than the analogous unsubstituted ester at the same loading levels. In some areas, the scores of the substituted compounds approach that of the control—no flame retardant present. U.S. Pat. No. 3,978,024 indicates that when a substituent is present, it should be an electron withdrawing group. All the substituents in this example and within the genus are election donating groups. The results of Table 2 are even more significant in view of this fact.

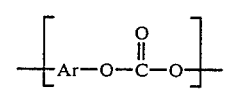

FORMULA I

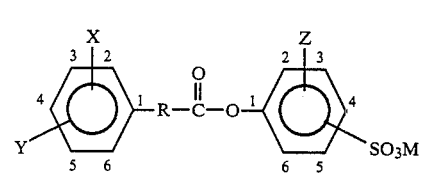

FORMULA II

-continued

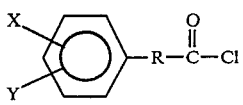
FORMULA IV

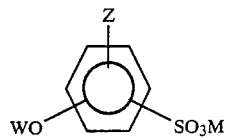
FORMULA V

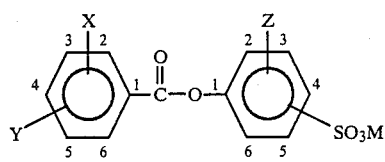
FORMULA VI

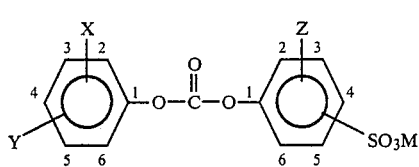
FORMULA VII

What is claimed is:

1. A composition which comprises a polymer having a repeating unit

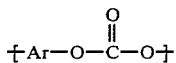

wherein Ar is an aromatic group in admixture with a flame retardant effective amount of a compound of the formula

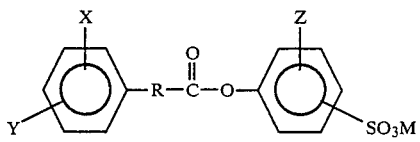

wherein
R is a valence bond or an oxa group;
M is an alkali or alkaline earth metal;
X, Y and Z are the same or different and are hydrogen, alkyl, alkenyl, cycloalkyl, aryl, alkaryl, aralkyl, and alkoxy with the proviso that at least one of X, Y and Z is other than hydrogen.

2. A composition in accordance with claim 1 wherein alkyl is one to about twelve carbon atoms, inclusive; alkenyl is two to about twelve carbon atoms, inclusive; cycloalkyl is of about five to eight carbon atoms, inclusive; aryl is phenyl; aralkyl is phenyl substituted alkyl of one to six carbon atoms, inclusive; alkaryl is alkyl substituted phenyl wherein alkyl is one to six carbon atoms, inclusive; and alkoxy is one to twelve carbon atoms, inclusive.

3. A composition in accordance with claim 2 wherein R is a valence bond.

4. A composition in accordance with claim 2 wherein R is an oxa group.

5. A composition in accordance with claim 2, 3 and 4 wherein the polymer is a homopolymer.

6. A composition in accordance with claim 5 wherein the aromatic group is derived from bisphenol-A.

7. A composition in accordance with claim 2 wherein M is potassium; R is a valence bond; SO₃M is at the 4-position; X and Z are hydrogen and Y is 2-methyl, 3-methyl, 4-methyl or 4-tert butyl.

8. A composition in accordance with claim 7 wherein y is 2-methyl.

9. A composition in accordance with claim 2 wherein M is potassium; R is an oxa group; SO₃M is at the 4-position; X and Z are hydrogen and Y is 4-tert butyl, 4-cumyl or 4-1,1,3,3-tetramethylbutyl.

10. A compound of the formula

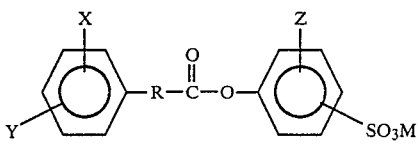

wherein
R is a valence bond or an oxa group;
M is an alkali or alkaline earth metal;
X, Y and Z are the same or different and are hydrogen, alkyl of one to about twelve carbon atoms, inclusive; alkenyl of two to about twelve carbon atoms, inclusive; cycloalkyl of about five to eight carbon atoms, inclusive; phenyl; phenyl substituted alkyl of one to six carbon atoms, inclusive; alkyl substituted phenyl wherein alkyl is one to six carbon atoms, inclusive; and alkoxy of one to twelve carbon atoms, inclusive, with the proviso that at least one of X, Y and Z is other than hydrogen.

11. A compound in accordance with claim 10 wherein M is an alkali metal.

12. A compound in accordance with claim 10 wherein R is a valence bond, SO₃M is at the 4-position; X and Z are hydrogen and Y is 2-methyl, 3-methyl, 4-methyl or 4-tert butyl.

13. A compound in accordance with claim 12 wherein Y is 2-methyl and M is potassium.

14. A compound in accordance with claim 12 wherein Y is 3-methyl and M is potassium.

15. A compound in accordance with claim 12 wherein Y is 4-methyl and M is potassium.

16. A compound in accordance with claim 12 wherein Y is 4-tert butyl and M is potassium.

17. A compound in accordance with claim 11 wherein R is an oxa group, SO₃M is at the 4-position, X and Z are hydrogen and Y is 4-tert butyl, 4-1,1,3,3-tetramethylbutyl or 4-cumyl.

18. A compound in accordance with claim 17 wherein Y is 4-tert butyl and M is potassium.

19. A compound in accordance with claim 17 wherein Y is 4-1,1,3,3-tetramethylbutyl and M is potassium.

20. A compound in accordance with claim 17 wherein Y is 4-cumyl and M is potassium.

* * * * *